(12) United States Patent
Fan et al.

(10) Patent No.: US 8,975,296 B2
(45) Date of Patent: Mar. 10, 2015

(54) FORMULATIONS FOR CATHEPSIN K INHIBITORS

(71) Applicant: Merck, Sharp & Dohme, Corp., Rahway, NJ (US)

(72) Inventors: Haihong Fan, Hatfield, PA (US); Majid Mahjour, Hatfield, PA (US); Justin Moser, Collegeville, PA (US); Bhagwant Rege, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/847,794

(22) Filed: Mar. 20, 2013

(65) Prior Publication Data

US 2013/0217766 A1 Aug. 22, 2013

Related U.S. Application Data

(63) Continuation of application No. 12/992,124, filed as application No. PCT/US2009/042924 on May 6, 2009, now abandoned.

(60) Provisional application No. 61/127,630, filed on May 14, 2008.

(51) Int. Cl.

| | |
|---|---|
| *A61K 31/275* | (2006.01) |
| *A61K 31/50* | (2006.01) |
| *A61K 31/501* | (2006.01) |
| *A61K 31/44* | (2006.01) |
| *A61K 47/38* | (2006.01) |
| *A61K 9/10* | (2006.01) |
| *A61K 9/20* | (2006.01) |
| *A61K 31/424* | (2006.01) |
| *A61K 47/32* | (2006.01) |

(52) U.S. Cl.
CPC . *A61K 47/38* (2013.01); *A61K 9/10* (2013.01); *A61K 9/2018* (2013.01); *A61K 9/2054* (2013.01); *A61K 31/424* (2013.01); *A61K 47/32* (2013.01); *A61K 31/44* (2013.01); *A61K 31/275* (2013.01); *Y10S 514/96* (2013.01); *Y10S 514/961* (2013.01)
USPC ...... 514/521; 514/252.01; 514/357; 514/960; 514/961

(58) Field of Classification Search
CPC .............................. A61K 31/275; A61K 31/44
USPC ...................... 514/521, 252.01, 357, 960, 961
See application file for complete search history.

(56) References Cited

U.S. PATENT DOCUMENTS

| | | | |
|---|---|---|---|
| 4,983,593 A | 1/1991 | Miyajima et al. | |
| 7,375,134 B2 * | 5/2008 | Bayly et al. | 514/521 |
| 2003/0232863 A1 | 12/2003 | Bayly et al. | |
| 2006/0009433 A1 | 1/2006 | Yao et al. | |
| 2007/0237818 A1 | 10/2007 | Malcolm et al. | |
| 2009/0318560 A1 | 12/2009 | Parent et al. | |

FOREIGN PATENT DOCUMENTS

| | | |
|---|---|---|
| EP | 0852140 B1 | 12/2003 |
| EP | 0901786 B1 | 6/2007 |
| WO | 2007/046842 A2 | 4/2007 |

OTHER PUBLICATIONS

Gauthier, et al., Bioorganic & Medicinal Chemistry Letters, vol. 18, No. 3 (2008), pp. 923-928, "The discovery of odanacatib (MK-0822), a selective inhibitor of cathepsin K".

Forster, et al., Journal of Pharmacy and Pharmacology, vol. 53, No. 3 (2001), pp. 303-315, "Characterization of glass solutions of poorly water-soluble drugs produced by melt extrusion with hydrophilic amorphous polymers".

Paradkar, et al., International Journal of Pharmaceutics, vol. 271, No. 1-2 (2004), pp. 281-285, "Characterization of currcumin-PVP solid dispersion obtained by spray drying".

Yamaguchi, T et al., Manuscript, Pfizer, Re: PC9674JTJ-EPO, vol. 53(4), pp. 221-228, "Improving the pharmaceutical properties of 4"-O-(4-methoxyphenyl) acetyltylosin by preparing solid dispersions with carboxymethyl ethyl cellulose", (1993).

Chiou, WL et al., Journal of Pharmaceutical Sciences, vol. 60, No. 9, pp. 1281-1302 (1971), "Pharmaceutical applications of solid dispersion systems".

Ford, JL, Pharm. Acta. Helv., vol. 61, No. 3, pp. 69-88 (1986), "The current status of solid dispersions".

\* cited by examiner

*Primary Examiner* — Kevin E Weddington
(74) *Attorney, Agent, or Firm* — Nicole M. Beeler; Catherine D. Fitch

(57) ABSTRACT

The instant invention relates to pharmaceutical compositions containing cathespin K inhibitors. Also disclosed are processes for making said pharmaceutical compositions.

9 Claims, No Drawings

FORMULATIONS FOR CATHEPSIN K INHIBITORS

BACKGROUND OF THE INVENTION

This invention relates to formulations of cathepsin K inhibitors.

A variety of cathepsin K inhibitors have been disclosed for the treatment of various disorders related to cathepsin K functioning, including osteoporosis, glucocorticoid induced osteoporosis, Paget's disease, abnormally increased bone turn over, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma. Representative examples of cathepsin K inhibitors include those disclosed in International Publication WO03/075836, which published on Sep. 18, 2003, to Merck & Co., Inc. & Axys Pharmaceuticals, which is hereby incorporated by reference in its entirety.

Cathepsin K inhibitors can be formulated for oral dosing as tablets, by using a direct compression, wet granulation or roller compaction method. Similarly, cathepsin K inhibitors can be formulated for oral dosing as gelatin capsules, being a liquid in a soft capsule, or dry powder or semi-solid in a hard capsule. In addition, cathepsin K inhibitors can be formulated for intravenous dosing.

The formulations of the instant invention have advantages over other formulations of cathepsin K inhibitors. Specifically, the formulations of the instant invention significantly improve the absorption of the cathepsin K inhibitor. The formulations of the instant invention also improve the bioavailability of the cathepsin K inhibitor and reduce the variability in exposure. Exposure can vary due to many factors, including whether the cathepsin K inhibitor is taken with or without food.

SUMMARY OF THE INVENTION

The instant invention relates to pharmaceutical compositions containing cathespin K inhibitors. The cathepsin K inhibitor solid dispersion formulations of the present invention are made by spray drying or hot melt extrusion processes. The cathepsin K inhibitor is combined with a polymer, thus forming an amorphous system after spray drying. The spray dried amorphous systems are made by combining 10-20% of the cathepsin K inhibitor with 80-90% polymer. The amorphous system is then combined with excipients to form tablets, or combined with water to form a suspension. Also disclosed are processes for making said pharmaceutical compositions.

DETAILED DESCRIPTION OF THE INVENTION

The cathepsin K inhibitor solid dispersion formulations of the present invention are made by spray drying or hot melt extrusion processes. The cathepsin K inhibitor is combined with a polymer, thus forming an amorphous system after spray drying. The spray dried amorphous systems are made by combining 10-20% of the cathepsin K inhibitor with 80-90% polymer. The amorphous system is then combined with excipients to form tablets, or combined with water to form a suspension.

A particularly effective cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide,

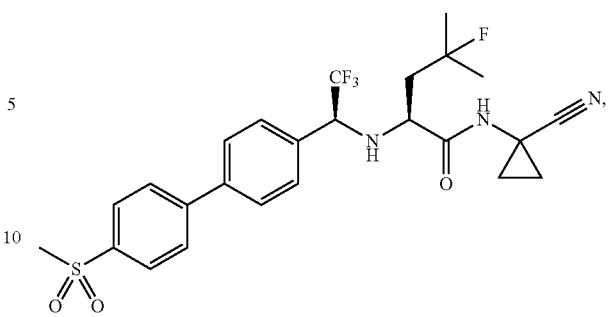

which can be prepared by procedures described in: International Publication WO03/075836, which published on Sep. 18, 2003, to Merck & Co., Inc. & Axys Pharmaceuticals; International Publication WO2006/017455, which published on Feb. 16, 2006, to Merck & Co., Inc.; U.S. Publication US2006-0052642, which published on Mar. 9, 2006; U.S. Publication US2005-0234128, which published on Oct. 20, 2005, to Merck & Co., Inc.; all of which are hereby incorporated by reference in their entirety. This compound is also known by its generic name, odanacatib.

The invention contemplates the use of any pharmaceutically acceptable fillers/compression aids, disintegrants, super-disintegrants, lubricants, binders, surfactants, film coatings, and solvents. Examples of these components are set forth below and are described in more detail in the Handbook of Pharmaceutical Excipients, Second Edition, Ed. A. Wade and P. J. Weller, 1994, The Pharmaceutical Press, London, England.

The instant invention comprises a pharmaceutical composition comprising from about 1% to 95% by weight of an amorphous cathepsin K inhibitor system, or a pharmaceutically acceptable salt thereof, and from about 5% to 99% by weight of excipients comprising a diluent, a glidant, a lubricant, a surfactant and a disintegrant. In a class of the instant invention, is a pharmaceutical composition comprising from about 44% to 57% by weight of an amorphous cathepsin K inhibitor system, or a pharmaceutically acceptable salt thereof, and from about 43% to 66% by weight of excipients comprising a diluent, a glidant, a lubricant, a surfactant and a disintegrant. In a class of the instant invention, is a pharmaceutical composition comprising about 50.0% by weight of an amorphous cathepsin K inhibitor system, or a pharmaceutically acceptable salt thereof, and about 50.0% by weight of excipients comprising a diluent, a polymer, a glidant, a lubricant, a surfactant and a disintegrant.

In an embodiment of the invention, the amorphous cathepsin K inhibitor system comprises a cathepsin K inhibitor and a polymer. Examples of the amorphous cathepsin K inhibitor systems of the instant invention include the spray dried material and the hot melt extrusion material.

In an embodiment of the invention, the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, or a pharmaceutically acceptable salt thereof.

In an embodiment of the invention, the polymer is hydroxypropyl methylcellulose acetate succinate (abbreviated as "HPMCAS"), copovidone (for example, Kollidon VA64), cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methyl acrylate-methacrylic acid copolymer, methacrylate-methacrylic or acid-octyl acrylate copolymer. The HPMCAS can be selected from HPMCAS-HF, HPMCAS-MF or HPMCAS-LF. HPMCAS-HF has an acetyl content of 10.0-14.0%, a succinoyl content of 4.0-8.0%, a methoxyl content of 22.0-26.0% and a hydroxypropoxyl content of 6.0-10.0%, with an average particle size of not more than 10 μm (available from ShinEtsu). HPMCAS-MF has an acetyl content of 7.0-11.0%, a succinoyl content of 10.0-14.0%, a methoxyl content of 21.0-25.0% and a hydroxypropoxyl content of 5.0-9.0%, with an average particle size of not more than 10 μm (available from ShinEtsu). HPMCAS-LF has an acetyl content of 5.0-9.0%, a succinoyl content of 14.0-18.0%, a methoxyl content of 20.0-24.0% and a hydroxypropoxyl content of 5.0-9.0%, with an average particle size of not more than 10 μm (available from ShinEtsu). In a class of the invention, the polymer is HPMCAS-HF.

In an embodiment of the invention, the amorphous cathepsin K inhibitor system comprises 10-20% of the cathepsin K inhibitor and 80-90% polymer. In a class of the invention, the amorphous cathepsin K inhibitor system comprises 10% of the cathepsin K inhibitor and 90% polymer. In another class of the invention, the amorphous cathepsin K inhibitor system comprises 15% of the cathepsin K inhibitor and 85% polymer. In another class of the invention, the amorphous cathepsin K inhibitor system comprises 20% of the cathepsin K inhibitor and 80% polymer.

In an embodiment of the invention, the cathepsin K inhibitor comprises 5.0 to 8.334% of the total tablet formulation. In a class of the invention, the cathepsin K inhibitor comprises 5.0% of the total tablet formulation. In another class of the invention, the cathepsin K inhibitor comprises 6.667% of the total tablet formulation. In another class of the invention, the cathepsin K inhibitor comprises 6.675% of the total tablet formulation. In another class of the invention, the cathepsin K inhibitor comprises 7.5% of the total tablet formulation.

In an embodiment of the invention, the diluents are selected from the group consisting of spray-dried lactose, lactose anhydrous, lactose monohydrate, mannitol, microcrystalline cellulose, calcium phosphate, calcium carbonate, magnesium carbonate and starch. In a class of the embodiment, the diluent is spray-dried lactose.

In an embodiment of the invention, the glidant, or flow aid, is silicone dioxide, colloidal silica, talc or starch. In a class of the invention, the glidant is silicone dioxide.

In an embodiment of the invention, the lubricant is magnesium stearate, stearic acid or sodium stearyl fumerate. In a class of the embodiment, the lubricant is magnesium stearate.

In an embodiment of the invention, the surfactant is sodium laurel sulfate, ammonium lauryl sulfate, another alkyl sulfate salt or poloxamer.

In an embodiment of the invention the disintegrant is croscarmellose sodium, starch, crospovidone, sodium starch glycolate or any mixtures thereof. In a class of the embodiment, the disintegrant is croscarmellose sodium.

The instant invention further comprises a method of improving the absorption of a cathepsin K inhibitor by combining the cathepsin K inhibitor with a polymer to form an amorphous system.

In an embodiment of the invention, the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, and the polymer is HPMCAS-HF.

The instant invention further comprises a method of reducing a food effect observed when dosing a cathepsin K inhibitor by combining the cathepsin K inhibitor with a polymer to form an amorphous system. In an embodiment of the invention, the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, and the polymer is HPMCAS-HF.

The instant invention further comprises a method of reducing variation in absorption observed when dosing a cathepsin K inhibitor by combining the cathepsin K inhibitor with a polymer to form an amorphous system. In an embodiment of the invention, the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, and the polymer is HPMCAS-HF.

The pharmaceutical tablet compositions of the present invention may also contain one or more additional formulation ingredients that may be selected from a wide variety of excipients known in the pharmaceutical formulation art. According to the desired properties of the tablet, any number of ingredients may be selected, alone or in combination, based upon their known uses in preparing tablet compositions. Such ingredients include, but are not limited to, diluents, binders, compression aids, disintegrants, lubricants, glidants, stabilizers (such as dessicating amorphous silica), flavors, flavor enhancers, sweeteners, preservatives, colorants and coatings.

The term "tablet" as used herein is intended to encompass compressed pharmaceutical dosage formulations of all shapes and sizes, whether uncoated or coated. Substances which may be used for coating include hydroxypropylmethylcellulose, hydroxypropylcellulose, titanium dioxide, talc, sweeteners and colorants.

The pharmaceutical compositions of the present invention are useful in the therapeutic or prophylactic treatment of disorders associated with cathpesin K functioning. Such disorders include: osteoporosis, glucocorticoid induced osteoporosis, Paget's disease, abnormal bone disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer, including metastatic bone disease, hypercalcemia of malignancy, and multiple myeloma.

The following examples are given for the purpose of illustrating the present invention and shall not be construed as being limitations on the scope of the invention.

Example 1

Preparation of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide (15% Drug Load in Spray Dried Material, 7.5% Drug Load in the Tablet Formulation)

| Ingredient | [%] | Amount (mg)/tablet |
| --- | --- | --- |
| 15% $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide 85% HPMC-AS-HF | 50.0 | 333.33 |
| Lactose, spray dried | 45.5 | 303.33 |
| Croscarmellose sodium | 3.0 | 20.00 |
| Cab-o-sil | 0.5 | 3.33 |
| Magnesium stearate | 1.0 | 6.67 |
| % Total | 100.0 | 666.67 |

The tablets were prepared by a dry granulation process. The N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide is combined with HPMC-AS-HF to form the spray dried material. The spray dried material was then blended with lactose, Croscarmelose sodium, cab-O-Sil and ½ of magnesium stearate and then dry granulated using a roller compaction equipment. The ribbon from the compaction was milled through a 1 mm screen. The milled granulation was blended for five minutes with the remaining of magnesium stearate. The 50 mg tablets were prepared using a tablet machine.

Example 2

Preparation of N$^1$-(1-Cyanocyclopropyl)-4-Fluoro-N$^2$-{(1S)-2,2,2-Trifluoro-1-[4'-(Methylsulfonyl)-1,1'-Biphenyl-4-Yl]Ethyl}-L-Leucinamide (15% Drug Load in Spray Dried Material, 6.667% Drug Load in the Tablet Formulation)

| Ingredient | [%] | Amount (mg)/tablet |
| --- | --- | --- |
| 15% N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide 85% HPMCAS-HF | 44.44 | 333.33 |
| Lactose, spray dried | 45.31 | 339.79 |
| Croscarmellose sodium | 6.00 | 45.00 |
| SLS | 2.00 | 15.00 |
| Cab-o-Sil | 1.00 | 7.50 |
| Magnesium stearate | 1.25 | 9.38 |
| % Total | 100.0 | 750.00 |

The tablets were prepared by a dry granulation process. The N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide is combined with HPMCAS-HF to form the spray dried material. The spray dried material was then blended with lactose, Croscarmelose sodium, sodium laurel sulfate, cab-O-Sil and ½ of magnesium stearate and then dry granulated using a roller compaction equipment. The ribbon from the compaction was milled through a 1 mm screen. The milled granulation was blended for five minutes with the remaining of magnesium stearate. The 50 mg tablets were prepared using a tablet machine.

Example 3

Preparation of N$^1$-(1-Cyanocyclopropyl)-4-Fluoro-N$^2$-{(1S)-2,2,2-Trifluoro-1-[4'-(Methylsulfonyl)-1,1'-Biphenyl-4-Yl]Ethyl}-L-Leucinamide (10% Drug Load in Spray Dried Material, 5% Drug Load in the Tablet Formulation)

| Ingredient | [%] | Amount (mg)/tablet |
| --- | --- | --- |
| 10% N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide 90% HPMCAS-HF | 50.0 | 500.00 |
| Lactose, spray dried | 20.125 | 201.25 |
| Avicel PH 102 | 20.125 | 201.25 |
| Croscarmellose sodium | 6.0 | 60.00 |
| SLS | 2.0 | 20.00 |
| Cab-o-Sil | 0.75 | 7.50 |
| Magnesium stearate | 1.0 | 10.00 |
| % Total | 100.0 | 1000 |

The tablets were prepared by a dry granulation process. The N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide is combined with/HPMCAS-HF to form the spray dried material. The spray dried material was then blended with lactose, Croscarmelose sodium, cab-O-Sil and ½ of magnesium stearate and then dry granulated using a roller compaction equipment. The ribbon from the compaction was milled through a 1 mm screen. The milled granulation was blended for five minutes with the remaining of magnesium stearate. The 50 mg tablets were prepared using a tablet machine.

Example 4

Preparation of N$^1$-(1-Cyanocyclopropyl)-4-Fluoro-N$^2$-{(1S)-2,2,2-Trifluoro-1-[4'-(Methylsulfonyl)-1,1'-Biphenyl-4-Yl]Ethyl}-L-Leucinamide (15% Drug Load in Hot Melt Extrusion Material, 6.675% Drug Load in the Tablet Formulation)

| Ingredient | [%] | Amount (mg)/tablet |
| --- | --- | --- |
| 15% N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide 10% Cremophor EL 75% Kollidon VA64 | 44.5 | 333.33 |
| Lactose, spray dried | 12.0 | 89.89 |
| Avicel PH 102 | 36.0 | 269.67 |
| Croscarmellose sodium | 6.0 | 44.94 |
| Cab-o-Sil | 0.5 | 3.75 |
| Magnesium stearate | 1.0 | 7.49 |
| % Total | 100.0 | 750.00 |

The tablets were prepared by a dry granulation process. The N$^1$-(1-cyanocyclopropyl)-4-fluoro-N$^2$-{(1S)-2,2,2-trifluoro-1-[4'-(methylsulfonyl)-1,1'-biphenyl-4-yl]ethyl}-L-leucinamide, Cremophor EL and Kollidon VA64 were combined to form the hot melt extrudet. The hot melt extrudet was then blended with lactose, Avicel PH102, Croscarmelose sodium, cab-O-Sil and ½ of magnesium stearate and then dry granulated using a roller compaction equipment. The ribbon from the compaction was milled through a 1 mm screen. The milled granulation was blended for five minutes with the remaining of magnesium stearate. The 50 mg tablets were prepared using a tablet machine.

Example 5

Preparation of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide (15% Drug Load in Spray Dried Material, 8.334% Total Drug Load in the Tablet Formulation)

| Ingredient | [%] | Amount (mg)/tablet |
|---|---|---|
| 15% $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide 85% HPMCAS-HF | 55.56 | 333.33 |
| Lactose, spray dried | 20.22 | 121.33 |
| Avicel PH 102 | 20.22 | 121.33 |
| Croscarmellose sodium | 3.00 | 18.00 |
| Magnesium stearate | 1.00 | 6.00 |
| % Total | 100.0 | 600.00 |

The tablets were prepared by a dry granulation process. The $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide was combined with HPMC-AS-HF to form the spray dried material. The spray dried material was then blended with lactose, Avicel PH102, Croscarmelose sodium, cab-O-Sil and ½ of magnesium stearate and then dry granulated using a roller compaction equipment. The ribbon from the compaction was milled through a 1 mm screen. The milled granulation was blended for five minutes with the remaining of magnesium stearate. The 50 mg tablets were prepared using a tablet machine.

Example 6

Preparation of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide (15% Drug Load in Spray Dried Material, 8.334% Total Drug Load)

| Ingredient | [%] | Amount (mg)/tablet |
|---|---|---|
| 15% $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide 85% HPMCAS-HF | 55.56 | 333.33 |
| Lactose, spray dried | 39.94 | 239.66 |
| Croscarmellose sodium | 3.00 | 18.00 |
| Cab-o-sil | 0.50 | 3.00 |
| Magnesium stearate | 1.00 | 6.00 |
| % Total | 100.0 | 600.00 |

The tablets were prepared by a dry granulation process. The $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide was combined with HPMC-AS-HF to form the spray dried material. The spray dried material was then blended with lactose, Croscarmelose sodium, cab-O-Sil and ½ of magnesium stearate and then dry granulated using a roller compaction equipment. The ribbon from the compaction was milled through a 1 mm screen. The milled granulation was blended for five minutes with the remaining of magnesium stearate. The 50 mg tablets were prepared using a tablet machine.

Example 7

Preparation of Suspension of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide (30 Mg/G)

| Component | Amount |
|---|---|
| 15% $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide 85% HPMCAS-HF | 15.0 g |
| Water | 60.0 g |

Suspension Preparation:

1. Weigh 15.0 g of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide and HPMCAS-HF in a defoamer container (size: 150 or 250 ml).
2. Add 60.0 g of water into the container; Shake gently to wet all the SD material.
3. Mix for 5 min using a defoamer and defoam for additional 5 min; Make sure a homogeneous suspension is formed.

Example 8

Preparation of Suspension of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide (20 Mg/G)

| Component | Amount |
|---|---|
| 15% $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide 85% HPMCAS-HF | 10.0 g |
| Water | 65.0 g |

Suspension Preparation:

1. Weigh 10.0 g of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide and HPMCAS-HF in a defoamer container (size: 150 or 250 ml).
2. Add 65.0 g of water into the container; Shake gently to wet all the SD material.

3. Mix for 5 min using a defoamer and defoam for additional 5 min; Make sure a homogeneous suspension is formed.

Example 9

Preparation of Suspension of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide (2.0 Mg/G)

| Component | Amount |
|---|---|
| 15% $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide 85% HPMCAS-HF | 1.00 g |
| Water | 74.0 g |

Suspension Preparation:
1. Weigh 1.00 g of $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide and HPMCAS-HF in a defoamer container (size: 150 or 250 ml).
2. Add 74.0 g of water into the container; Shake gently to wet all the SD material.
3. Mix for 5 min using a defoamer and defoam for additional 5 min; Make sure a homogeneous suspension is formed.

Example 10

Preparation of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide 50 Mg Tablets

| Ingredient | % wt./wt. | Mg/Tablet |
|---|---|---|
| $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide | 12.5 | 50.00 |
| Microcrystalline Cellulose | 40 | 160.00 |
| Lactose Monohydrate | 40 | 160.000 |
| Croscarmellose Sodium | 4 | 16.00 |
| Hydroxypropyl cellulose | 3 | 12.00 |
| Magnesium Stearate | 0.5 | 2.00 |
| Purified Water* | [35] | [140.00] |
| Total | 100 | 400.00 |

*removed during the during process $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, 4% (wt./wt.) croscarmellose sodium, and a 1:1 (wt./wt.) mixture of microcrystalline cellulose and lactose monohydrate are dry blended in a high shear mixer, and then a 3% (wt./wt.) hydroxypropyl cellulose solution is sprayed onto the mixing powders to effect granulation. The wet granulate is dried in a fluid bed dryer, the dried granulate is then milled, and finally lubricated with 0.5% (wt./wt.) magnesium stearate in a blender. Tablets were then compressed on a rotary tablet press.

Example 11

Mean (Se) Pk Parameters after Oral Administration of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide Solid Tablets (10 Mg Dose/Animal) in Fasted Male Beagle Dogs

| Formulation | Dose (mg) | $AUC_{0-72hr}$ (μM*hr) | $AUC_{0-24hr}$ (μM*hr) | $C_{max}$ (μM) | $T_{max}$ (hr) |
|---|---|---|---|---|---|
| Example 10 | 10 | N/A | 7.3 (3.6) | 0.46 (0.14) | 4 (0.5, 4) |
| Example 2 | 10 | N/A | 59.6 (5.2) | 3.93 (0.10) | 4 (4, 4) |
| Example 3 | 10 | 178.0 (38.2) | 70.6 (16.2) | 4.0 (0.8) | 2 (2, 8) |
| Example 4 | 10 | 41.8 (11.8) | 16.8 (4.0) | 0.9 (0.2) | 8 (8, 24) |

Animal studies in beagle dogs were conducted to evaluate the formulations. In general, the formulations containing the spray dried material (Examples 2 and 3) provided ~8-10 fold higher exposures compared to the formulation that does not contain the spray dried material or hot melt extrusion and ~5 folds higher than the hot melt extrusion (Example 4). Similarly, the formulation containing the hot melt extrusion material (Example 4) increased the exposure by about 2.3 folds higher exposure compared to the standard formulation (Example 10).

Example 12

Mean (Se) Pk Parameters after Oral Administration of $N^1$-(1-Cyanocyclopropyl)-4-Fluoro-$N^2$-{(1S)-2,2,2-Trifluoro-1-[4'-(Methylsulfonyl)-1,1'-Biphenyl-4-Yl]Ethyl}-L-Leucinamide Solid Tablets (10 Mg Dose/Animal) in Fasted/Fed Male Beagle Dogs

| Formulation | Feeding Conditions (10 mg dose) | $AUC_{0-24hr}$ (μM*hr) | $C_{max}$ (μM) | $T_{max}$ (hr) | $AUC_{Fed/Fasted}$ |
|---|---|---|---|---|---|
| Example 10 | Fasted | 7.3 (3.6) | 0.46 (0.14) | 4 (0.5, 4) | 4.3 |
|  | Fed (high fat) | 31.4 (6.1) | 1.77 (0.40) | 8 (8, 8) |  |
| Example 2 | Fasted | 59.6 (5.2) | 3.93 (0.10) | 4 (4, 4) | 1.2 |
|  | Fed (high fat) | 73.0 (8.3) | 4.27 (0.41) | 6 (6, 8) |  |

A significant food effect was observed with the formulation that does not contain the spray dried material. The formulation containing the spray dried material (Example 2) helped to minimize the variability in exposure.

What is claimed is:
1. A pharmaceutical composition comprising from 1% to 95% by weight of an amorphous cathepsin K inhibitor system and from 5% to 99% by weight of excipients comprising a diluent, a glidant, a lubricant, a surfactant and a disintegrant, wherein the amorphous cathepsin K inhibitor system comprises a cathepsin K inhibitor, which is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, and a polymer selected from the group consisting of HPMCAS, copovidone, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, methacrylate-methacrylic and acid-octyl acrylate copolymer.

2. The pharmaceutical composition of claim 1 comprising from 44% to 57% by weight of an amorphous cathepsin K inhibitor system and from 43% to 66% by weight of excipients comprising a diluent, a glidant, a lubricant, a surfactant and a disintegrant.

3. The pharmaceutical composition of claim 2 comprising 50.0% by weight of an amorphous cathepsin K inhibitor system and 50.0% by weight of excipients comprising a diluent, a glidant, a lubricant, a surfactant and a disintegrant.

4. The pharmaceutical composition of claim 1 wherein the polymer is selected from the group consisting of HPMCAS and copovidone.

5. The pharmaceutical composition of claim 4 wherein the polymer is selected from the group consisting of HPMCAS-HF, HPMCAS-MF, HPMCAS-LF and Kollidon VA64.

6. The pharmaceutical composition of claim 5 wherein the polymer is HPMCAS-HF.

7. The pharmaceutical composition of claim 6 wherein the diluent is spray-dried lactose, the glidant is silicone dioxide, the lubricant is magnesium stearate, the surfactant is sodium laurel sulfate, and the disintegrant is croscarmellose sodium.

8. A method of improving the absorption of a cathespin K inhibitor by combining the cathepsin K inhibitor with a polymer to form an amorphous system, wherein the cathepsin K inhibitor is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, and the polymer is selected from the group consisting of HPMCAS, copovidone, cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic mono-ester copolymer, methyl acrylate-methacrylic acid copolymer, methacrylate-methacrylic and acid-octyl acrylate copolymer.

9. The method of claim 8 wherein the cathepsin K inhibitor is is $N^1$-(1-cyanocyclopropyl)-4-fluoro-$N^2$-{(1S)-2,2,2-trifluoro-1-[4'-(methylsulfonyl)-1,1'-biphenyl-4-yl]ethyl}-L-leucinamide, and the polymer is HPMCAS-HF.

* * * * *